United States Patent [19]
Longo et al.

[11] Patent Number: 5,534,428
[45] Date of Patent: Jul. 9, 1996

[54] CLONED SSTI/SACI RESTRICTION-MODIFICATION SYSTEM

[75] Inventors: Mary C. Longo, Germantown; Michael D. Smith, Rockville, both of Md.; Raymond D. Harris, Falkirk, Scotland

[73] Assignee: Life Technologies, Inc., Gaithersburg, Md.

[21] Appl. No.: 300,226

[22] Filed: Sep. 6, 1994

[51] Int. Cl.$^6$ ............... C12N 9/22; C12N 15/55; C12N 15/70

[52] U.S. Cl. .......... 435/199; 435/193; 435/252.33; 536/23.2

[58] Field of Search ............... 435/199, 193, 435/252.33; 536/23.2

[56] References Cited

U.S. PATENT DOCUMENTS

| | | | |
|---|---|---|---|
| 5,192,675 | 3/1993 | Chatterjee et al. | 435/199 |
| 5,288,696 | 2/1994 | Guthrie et al. | 435/199 |
| 5,334,526 | 8/1994 | Smith et al. | 435/199 |

OTHER PUBLICATIONS

Blumenthal et al., "Cloning of a Restriction–Modification System from *Proteus vulgaris* and Its Use in Analyzing a Methylase-Sensitive Phenotype in *Escherichia coli*," *J. Bacteriol.* 164:501–509 (Nov. 1985).
Bougueleret et al., "Characterization of the genes coding for the *Eco* RV restriction and modification system of *Escherichia coli*," *Nucl. Acids Res.* 12:3659–3676 (1984).
Brooks et al., "Cloning the BamHI restriction modification system," *Acids Res.* 17:979–997 (1989).
Gingeras & Brooks, "Cloned restriction/modification system from *Pseudomonas aeruginosa*," *PNAS* 80:402–406 (Jan. 1983).
Goff & Rambach, "SstI: A Restriction Endonuclease from *Streptomyces sp.* stanford," *Gene* 3:347–352 (1978).
Greene et al., "Sequence Analysis of the DNA Encoding the *Eco* RI Endonuclease and Methylase," *J. Biol. Chem.* 256:2143–2151 (Mar. 10, 1981).
Hammond et al., "Cloning the *KpnI* restriction–modification system in *Escherichia coli*," *Gene* 97:97–102 (1990).
Heitman & Model, "Site-Specific Methylases Induce the SOS DNA Repair Response to *Escherichia coli*," *J. Bacteriol.* 169:3243–3250 (Jul. 1987).
Howard et al., "Cloning the *Dde*I restriction–modification system using a two-step method," *Nucl. Acids Res.* 14:7939–7951 (1986).
Janulaitis et al., "Cloning of the modification methylase gene of *Bacillus centrosporus* in *Escherichia coli*," *Gene* 20:197–204 (1982).
Kiss & Baldauf, "Molecular cloning and expression in *Escherichia coli* of two modification methylase genes of *Bacillus subtilis*," *Gene* 21:111–119 (1983).
Kosykh et al., "Molecular Cloning of *Eco*RII Endonuclease and Methylase Genes," *Mol. Gen. Genet.* 178:717–718 (1980).
Lisser & Margalit, "Compilation of *E. coli* mRNA promoter sequences," *Nucl. Acids Res.* 21:1507–1516 (1993).

Mann et al., "Cloning of Restriction and Modification Genes in *E. coli:* The *Hha*II System from *Haemophilus haemolyticus*," *Gene* 3:97–112 (1978).
Newman et al., "DNA Sequences of Structural Genes for *Eco*RI DNA Restriction and Modification Enzymes," *J. Biol. Chem.* 256:2131–2139 (Mar. 10, 1981).
Post et al., "DNA Sequences of Promoter Regions for the *str* and *spc* Ribosomal Protein Operons in *E. coli*," *Cell* 15:215–229 (Sep. 1978).
Raleigh & Wilson, "*Escherichia coli* K–12 restricts DNA containing 5-methylcytosine," *PNAS* 83:9070–9074 (Dec. 1986).
Reddy et al., "Hyperexpression and purification of *Escherichia coli* adenylate cyclase using a vector designed for expression of lethal gene products," *Nucl. Acids Res.* 17:10473–10488 (1989).
Revel, H., "Restriction of Nonglucosylated T-even Bacteriophage: Properties of Permissive Mutants of *Escherichia coli* B and K12," *Virology* 31:688–701 (1967).
Rodicio & Chater, "Cloning and expression of the *Sal*I restriction–modification genes of *Streptomyces albus* G," *Mol. Gen. Genet.* 213:346–353 (1988).
Rosenberg & Court, "Regulatory sequences involved in the promotion and termination of RNA transcription," *Ann. Rev. Genet.* 13:319–353 (1979).
Szomolányi et al., "Cloning the modification methylase gene of *Bacillus sphaericus* R in *Escherichia coli*," *Gene* 10:219–225 (1980).
Walder et al., "Cloning and expression of the *Pst*I restriction–modification system in *Escherichia coli*," *PNAS* 78:1503–1507 (Mar. 1981).
Walder et al., "Cloning of the Msp*I* Modification Enzyme," *J. Biol. Chem.* 258:1235–1241 (Jan. 25, 1983).
Wilson, G. G., "Cloned restriction–modification systems—a review," *Gene* 74:281–289 (1988).
Zhuravleva et al., "Isolation and Purification of Restriction Endonuclease Sac 1 from *Streptomyces achromogenes* ATCC 12767," *Prikl. Biokhim. Mikrobiol.* 23:208–215 (1987).
Mjsklija, D. et al. (1991) Mol. Gen. Genet., 229, 119–128.
Ikemura, T., et al. (1979) Cell 18, 895–903.

*Primary Examiner*—Charles L. Patterson, Jr.
*Attorney, Agent, or Firm*—Sterne, Kessler, Goldstein & Fox

[57] ABSTRACT

The present invention discloses the cloning and expression in *Escherichia coli* of the SstI/SacI restriction-modification system. The SstI methylase gene was cloned by methylase selection (the "Hungarian Trick") and the orientation and boundaries of the gene were established. The level of methylation of the host was improved significantly by expressing the SstI methylase from the strong RPSL promoter. Using the SstI methylase clone as a probe, a chromosomal map was generated in the area of the gene for the SstI methylase. DNA downstream from the methylase was cloned and found to contain the gene for the SstI endonuclease. The orientation of the SstI endonuclease was established and a strong promoter was placed close to the SstI endonuclease gene by generating nested deletions. By these methods, an *E. coli* strain was constructed which produced high levels of SstI endonuclease. The SacI locus in the *S. achromogenes* chromosome was found to be identical to the SstI locus in *S. stanford* in all measured respects.

20 Claims, 10 Drawing Sheets

CLONED SSTI/SACI RESTRICTION-MODIFICATION SYSTEM

BACKGROUND OF THE INVENTION

1. Field of the Invention

The present invention is in the field of genetic engineering and molecular biology. It concerns production of proteins, specifically the restriction endonucleases SstI and SacI, in a heterologous organism from a gene carried by a recombinant DNA molecule.

2. Background of the Invention

There has been much effort to clone restriction-modification systems. The first cloning of a DNA endonuclease gene was described by Mann, M. B. et al., *Gene* 3:97–112 (1978). Since then more than seventy DNA methylase and restriction endonucleases have been cloned, the majority of the restriction endonuclease genes being closely linked to its corresponding methylase gene. Cloning of such genes allows one to produce large quantities of an enzyme.

Several methods by which restriction-modification systems can be cloned have been described. A number of endonuclease and methylase genes have been cloned from endogenous plasmids: EcoRII (Kosykh, V. B. et al., *Mol. Gen. Genet.* 178:717–718 (1980)), EcoRI (Newman, A. K. et al., *J. Biol. Chem.* 256:2131–2139 (1981)), Greene, P. J. et al., *J. Biol. Chem.* 256:2143–2153 (1981)), EcoRV (Bougueleret, L. et al., *Nucl. Acids Res.* 12:3659–3676 (1984)), PvuII (Blumenthal, R. M. et at., *J. Bacteriol.*164:501–509 (1985)), and PaeR71 (Gingeras & Brooks, *Proc. Natl. Acad. Sci. USA* 80:402–406 (1983)). Other methods of cloning include a phage restriction method in which bacterial cells carrying cloned restriction and modification genes will survive phage infection (Mann et al. supra; Walder, R. Y. et al., *Proc. Natl. Acad. Sci. USA* 78:1503–1507 (1981); Rodicio & Chater, *Mol. Gert. Genet.* 213:346–353 (1988)), and a procedure based on methylation protection suggested by Mann et at., supra, and Szomolanyi, E. et al., *Gene* 10:219–225 (1980). This latter scheme involves digestion of a plasmid library with the restriction enzyme to be cloned so that only plasmids whose sequences are modified, because of the presence of the methylase, will produce transformants in a suitable host. This selection has worked well to clone endonuclease and methylase genes together as well as methylase genes alone (Szomolanyi et at., supra; Janulaitis, A. et at., *Gene* 20:197–204 (1982); Walder, R. Y. et at., *J. Biol. Chem.* 258:1235–1241 (1983); Kiss & Baldanf, *Gene* 21:111–119 (1983); Wilson, G. G., *Gene* 74:281–289 (1988)). However, this technique sometimes yields only the methylase gene, even though the endonuclease and modifying genes are closely linked, as in the case of KpnI (Hammond, A. W. et at., *Gene* 97:97–102 (1990)).

Cloning of certain restriction-modification systems in *E. coli*, including DdeI (Howard, K. A. et al., *Nucl. Acids Res.* 14:7939–7950 (1989)), BamHI (Brooks, J. E. et al., *Nucl. Acids Res.* 17:979–997 (1989)), KpnI (Hammond, A. W. et at., supra) has required a multi-step approach. In each case, protection of the host with methylase expressed on a plasmid was necessary to stabilize a compatible vector containing the functional endonuclease gene. A head-start model to explain why some restriction-modification systems must be cloned utilizing a protected host was proposed by Wilson, supra. This model states that in order to establish a plasmid carrying a restriction-modification system, methylase protection must be faster than endonuclease digestion. Otherwise, the restriction enzyme would cleave unmethylated plasmid and/or genomic DNA and degrade the plasmid and/or kill the host. Although this model is a plausible explanation of plasmid establishment, it has not been determined previously whether continued independent expression of methylase from a separate plasmid is necessary to maintain the plasmid carrying the restriction-modification system during cell growth and replication.

Restriction endonucleases are named according to the names of the microorganisms that produce them. Microorganisms, in turn, have been named according to a wide variety of criteria, including morphology, biochemical characteristics and 16S ribosomal RNA patterns. Occasionally, two microorganisms are given different names when they are actually very similar if not identical organisms. A *Streptomyces stanford* strain which makes restriction enzymes SstI and SstII (ATCC29415), and a *Streptomyces achromogenes* strain (ATCC12767) which makes restriction enzymes SacI and SacII have identical chromosomal digestion patterns in the area of the SstI locus (see below) and indistinguishable overall digestion patterns when digested with each of several restriction enzymes. It thus appears that they are very similar, if not identical organisms and that the SstI locus and the SacI locus are either very similar or identical.

SUMMARY OF THE INVENTION

The present invention relates to a recombinant DNA molecule comprising:

(a) a vector, and (b) a structural gene encoding SstI or Sad restriction endonuclease wherein the structural gene is linked to the vector, whereby the structural gene may be maintained in a cell by the vector.

The present invention further relates to a method of producing a restriction endonuclease where the restriction endonuclease gene cannot be obtained by methylase selection comprising, in series, the steps of (A) growing a cell containing
  (1) a first DNA molecule comprising
    (a) a structural gene encoding a resrtiction endonuclease
    (b) a promoter,
  wherein the promoter is linked to the structural gene, and
  wherein the promoter is in such position and orientation with respect to the structural gene that the structural gene is expressed under control of the promoter,
  whereby the endonuclease protein encoded by the structural gene is expressed under control of the promoter, and
  (2) a second DNA molecule comprising
    (c) a restriction modification methylase gene,
  wherein the methylase gene is linked to a heterologous promoter, and
  wherein the methylase gene protects the DNA contained by a host cell from degradation by the endonuclease, and (B) extracting the endonuclease from the cell of step (A), whereby the endonuclease is produced.

The invention further relates to a method of producing a restriction endonuclease comprising, in series, the steps of (A) simultaneously transforming a cell with
  (1) a first DNA molecule comprising (a) a structural gene encoding a restriction endonuclease (b) a promoter, wherein the promoter is linked to the structural gene, and wherein the promoter is in such position and orientation with respect to the structural gene that the structural gene is expressed under control of the promoter, whereby the endonuclease protein encoded by the structural gene is expressed under control of the promoter, and (2) a second DNA molecule comprising (c) a restriction modification methylase gene, wherein the methylase gene is linked to a promoter, and wherein the methylase gene is capable of protecting DNA contained by a host cell from degradation by said endonuclease, (B) growing said transformed cell, and (C) extracting said endonuclease from the cell of step (A), whereby said endonuclease is produced.

The invention further provides a DNA molecule comprising a ribosomal protein small subunit 1 (rps 1) promoter operably linked to a heterologous structural gene.

The invention also provides a cell, wherein the cell contains a SstI or SacI endonuclease structural gene and the cell is not of the genus Streptomyces.

The SstI and SacI restriction endonucleases recognize and cleave the sequence 5' GAGCT^C 3'("^" indicates the site of cutting); the exact specificity of the SstI and SacI methylases is unknown. The present invention discloses the cloning and expression in E. coli of the SstI restriction-modification system, and the demonstration that the SstI and SacI RM systems are very similar if not identical. Although the SstI endonuclease and methylase genes were closely linked, initial attempts using a prior art method to clone both genes as a single DNA fragment in a plasmid vector failed to produce a clone in which both genes were present.

Initial cloning in E. coli of the SstI methylase was attempted by a variation of the "Hungarian Trick" in which a cloning vector was specifically constructed to clone the SstI methylase. The degree of methylation by the SstI methylase was not complete, even when the gene was cloned on a high copy plasmid under the control of the lac promoter. Accordingly, the insert containing the SstI methylase gene was trimmed of extraneous DNA, and the methylase gene was cloned under strong promoter control (the RPSL promoter) in a multicopy plasmid.

The SstI methylase clone was used to map the SstI locus and to generate subsequent SstI clones by cloning and hybridization. The gene for the SstI endonuclease was cloned under lac promoter control, and a small amount of SstI endonuclease activity was detected. The orientation of the SstI endonuclease gene was determined by subcloning, and extraneous DNA was trimmed away from the insert. This strain thus created produces approximately four hundred thousand units of SstI endonuclease per gram wet weight of cells. This is considerably more than the level of SstI produced by Streptomyces stanford, and the enzyme is easier to purify from the E. coli strain since it will not produce SstII as the S. stanford strain does.

It was demonstrated that the SstI locus in S. stanford ATCC29415 is indistinguishable from the SacI locus in Streptomyces achromogenes ATCC12767. Thus, the method used here to clone the SstI gene is easily used to clone the SacI system.

DEFINITIONS

Figure 1A:
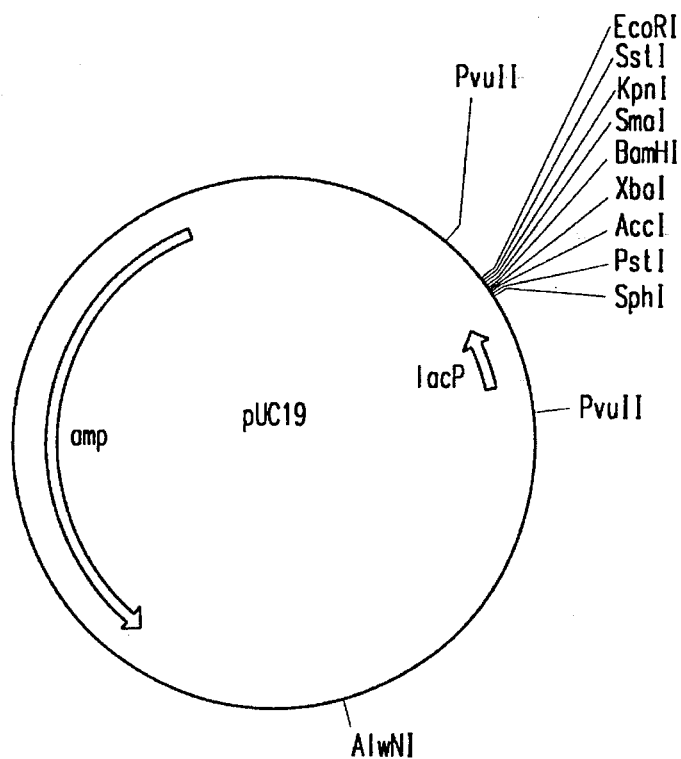
FIGS. 1a, 1b, 1c, 1d and 1e present the plasmid maps of cloning vectors pUC19 (FIG. 1a), pTTQ19 (FIG. 1b), pGEM-7Zf (FIG. 1c), pSU50 (FIG. 1d) and pSLKS101 (FIG. 1e). Ampicillin resistance genes (amp), kanamycin resistance genes (kan), lac repressor genes (lacI), lac promoter sequences (lacP), tac promoter sequences (tacP) and rpsl promoter sequences (rpslP) are marked. The construction of pSLKS101 is described in Example 1.3.

In the description that follows, a number of terms used in recombinant DNA technology are utilized extensively. In order to provide a clear and consistent understanding of the specification and claims, including the scope to be given such terms, the following definitions are provided.

Cloning vector.

A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector.

A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Substantially pure.

As used herein means that the desired purified enzyme is essentially free from contaminating cellular components, said components being associated with the desired enzyme in nature, as evidenced by a single band following polyacrylamide-sodium dodecyl sulfate gel electrophoresis. Contaminating cellular components may include, but are not limited to, phosphatases, exonucleases or other undesirable endonucleases.

Restriction endonuclease isoschizomer

A restriction endonuclease isoschizomer is a term used to designate a group of restriction endonucleases that recognize and bind to the same recognition sequence but are isolated from different microbial sources. Restriction endonuclease isoschizomers may or may not cleave in the exact location as the restriction endonuclease with which it is being compared.

Modification methylase isoschizomer.

A modification methylase isoschizomer is a term used to designate a group of modification methylases that recognize the same recognition sequence but are isolated from different microbial sources. Modification methylase isoschizomers may or may not chemically modify the same nucleotides within the recognition sequence as the restriction endonuclease with which it is being compared.

Recognition sequence.

Recognition sequences are particular DNA sequences which a restriction endonuclease or a modification methylase recognizes and binds. Recognition sequences are typically four to six (and in some cases, eight) nucleotides in length with a two-fold axis of symmetry.

Recombinant Host.

According to the invention, a recombinant host may be any prokaryotic or eukaryotic microorganism which contains the desired cloned genes on an expression vector or cloning vector. This term is also meant to include those microorganisms that have been genetically engineered to contain the desired gene(s) in the chromosome or genome of that organism. The term "recombinant host" is not meant to include the wild type Streptomyces strain which produces SstI or SacI.

Recombinant vector.

Any cloning vector or expression vector which contains the desired cloned gene(s).

Promoter.

A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Gene.

A DNA sequence that contains information needed for expressing a polypeptide or protein.

Structural gene.

A DNA sequence that is transcribed into messenger RNA (mRNA) that is then translated into a sequence of amino acids characteristic of a specific polypeptide.

Expression.

Expression is the process by which a polypeptide is produced from a structural gene. The process involves transcription of the gene into mRNA and the translation of such mRNA into polypeptide(s).

Heterologous structural gene.

A gene coding for a protein other than the ribosomal protein small subunit 1 (rps 1), e.g. a gene coding for a restriction enzyme or modification methylase, an antigen, an enzyme, a blood factor, an adhesion protein, a transport protein or other prokaryotic or eukaryotic protein.

Strong prokaryotic promoter.

A promoter which drives expression of a modification methylase gene to which it is operably linked at a level which protects the host DNA from cleavage and which protects the host from death when the modification methylase and restriction endonuclease genes are transformed into a host substantially simultaneously.

DETAILED DESCRIPTION OF THE PREFERRED EMBODIMENTS

This invention is directed to recombinant hosts which express the gene coding for the restriction endonuclease SstI or SacI and to DNA molecules which contain the gene. More specifically, the invention is directed to a recombinant DNA molecule comprising a vector and a structural gene encoding SstI or SacI restriction endonuclease, wherein the structural gene is linked to the vector, whereby the structural gene may be maintained in a cell by the vector. In a preferred embodiment the molecule, further comprises a promoter, wherein the promoter is linked to the structural gene and the vector, whereby the promoter may be maintained in a cell by the vector, and wherein the promoter is in such position and orientation with respect to the structural gene that the structural gene may be expressed under control of the promoter, whereby the SstI or SacI endonuclease protein encoded by the structural gene may be expressed under control of the promoter. In another preferred embodiment, the promoter is a SstI or SacI endonuclease gene promoter.

This present invention is further directed to gene(s) coding for the modification methylase genes which are complementary to the SstI or SacI restriction ehdonuclease. These methylases chemically modify certain nucleotides with the recognition sequence by the addition of a methyl group, thus making the modified sequence resistant to cleavage by the complementary restriction endonuclease. More specifically, the invention provides a molecule as described above further comprising a SstI or SacI restriction modification methylase gene, wherein the methylase gene is linked to the structural gene and the vector, whereby the methylase gene may be maintained in a cell by the vector, and wherein the methylase gene is capable of protecting DNA contained by a host cell from degradation by SstI or SacI endonuclease.

In another embodiment, the present invention provides methods for producing the enzymes of the invention, for example, a method of producing a restriction endonuclease comprising, in series, the steps of (A) growing a cell containing
  (1) a first DNA molecule comprising
    (a) a structural gene encoding a restriction endonuclease
    (b) a promoter,
  wherein the promoter is linked to the structural gene, and
  wherein the promoter is in such position and orientation with respect to the structural gene that the structural gene is expressed under control of the promoter,
  whereby the endonuclease protein encoded by the structural gene is expressed under control of the promoter, and
  (2) a second DNA molecule comprising
    (c) a restriction modification methylase gene,
  wherein the methylase gene is linked to a heterologous promoter, and wherein the methylase gene is capable of protecting DNA contained by a host cell from degradation by the endonuclease expressed by the structural gene of the first DNA molecule, and (B) extracting the endonuclease from the cell of step (A), whereby the endonuclease is produced.

In another embodiment, the present invention provides a method of producing a restriction endonuclease comprising, in series, the steps of (A) simultaneously transforming a cell with
(1) a first DNA molecule comprising
(a) a structural gene encoding a restriction endonuclease
(b) a promoter, wherein the promoter is linked to the structural gene, and wherein the promoter is in such position and orientation with respect to the structural gene that the structural gene is expressed under control of the promoter, whereby the endonuclease protein encoded by the structural gene is expressed under control of the promoter, and (2) a second DNA molecule comprising
(c) a restriction modification methylase gene, wherein the methylase gene is linked to a promoter, and wherein the methylase gene is capable of protecting DNA contained by a host cell from degradation by said endonuclease, (B) growing said transformed cell, and (C) extracting said endonuclease from the cell of step (A), whereby said endonuclease is produced.

In an preferred embodiment, the first DNA molecule and the second DNA molecules are pan of different expression vectors.

In a further preferred embodiment, the cell is *E. coli* DH10B Rec$^+$ (pSst12) (pSst16) deposited on Aug. 23, 1994 as NRRL B-21313 with the Agricultural Research Service Patent Culture Collection, Northern Regional Research Center, 1815 N. University St., Peoria, Ill. 61604.

In another preferred embodiment, the first DNA molecule and the second DNA molecule are part of the same expression vector. In a further preferred embodiment, the method as described above, further comprises after step (C) the step of (D) purifying the endonuclease.

In another preferred embodiment, the restriction endonuclease is a SstI or SacI restriction endonuclease. In a further preferred embodiment, the methylase gene is a SstI or SacI methylase gene. In another preferred embodiment, the promoter linked to the methylase gene is a heterologous promoter. In a most preferred embodiment, the promoter is a strong, heterologous promoter which drives the expression of the modification methylase to give a concentration sufficient to protect host DNA the cleavage by the expressed endonuclease and, thus, the death of the cell.

Also provided by this invention are recombinant hosts and DNA molecules which contain genes coding for isoschizomers of the restriction endonuclease and modification methylase of the present invention. In one preferred embodiment, the host contains a SstI or SacI endonuclease structural gene and the host is not of the genus Streptomyces. In one preferred embodiment, the host is an *E. coli* cell.

The restriction endonuclease SstI or SacI and its corresponding modification methylase may be obtained from any strain of Streptomyces. Genes coding for isoschizomers of these enzymes can be obtained from any genus including, but not limited to, Arthrobacter, Bacillus, Citrobacter, Enterobacter, Escherichia, Havobacterium, Caryophanon, Klebsiella, Micrococcus, Neisseria, Xanthomonas, Nocardia, Pseudomonas, Salmonella, and Streptomyces.

DNA molecules which code for SstI/SacI and SstI/SacI methylase, or isoschizomers thereof, can be recombined into a cloning vector and introduced into a host cell to enable the expression of the restriction endonuclease or modification methylase by that cell. DNA molecules may be recombined with vector DNA in accordance with conventional techniques, including restriction digestion to provide appropriate termini, filling in of cohesive ends as appropriate, alkaline phosphatase treatment to avoid undesirable joining, and ligation with appropriate ligases.

Nomenclature for naming restriction endonucleases are in accord with the proposal of Smith et al., *J. Mol. Biol.* 81:419–423 (1973). Briefly, the first letter "S" of SstI designates the genus "Streptomyces" while the lower case letters "st" designate the species "stanford." Thus, the original strain found to produce SstI was designated *Streptomyces stanford*.

The standard method for cloning restriction endonuclease genes and genes of their DNA-protecting methylases relies on the proximity of the two genes to each other and on the expression of both genes in *E. coli*. This method has been termed "methylase selection."

The first step of this process is to select for methylase-producing clones (the "Hungarian Trick"). A vector having one or, preferably, more cleavage sites of the restriction enzyme to be cloned is chosen. Partial digestion conditions are used to fragment genomic DNA from the producing organism, so that one avoids always cutting in the middle of a gene. A library of clones is prepared with these chromosomal fragments present as inserts in the chosen vector. After this library has been transformed into *E. coli*, DNA is isolated from the pool of transformants. The DNA isolated is a mixture of different molecules, having virtually all possible inserts. The vector/insert combinations having a methylase gene will have methylated endonuclease cleavage sites if the methylase is expressed in *E. coli*. The isolated DNA is next digested with the appropriate restriction enzyme. Unmethylated vector/insert combinations are degraded and methylated combinations survive the endonuclease treatment. The endonuclease-treated DNA is then transformed into *E. coli*. Degraded combinations do not become established. Methyl-protected combinations, which survived the endonuclease treatment, can establish and maintain themselves in the new *E. coli* host cells, thereby forming clones.

The clones are then screened for expression of the endonuclease gene. Cell extracts of these clones are then assayed for restriction endonuclease activity, thus identifying clones expressing the restriction enzyme. Thus, genes for a restriction methylase and endonuclease system can be cloned on a single recombinant DNA molecule, the restriction endonuclease being used to select DNA molecules carrying the gene of its methylase.

There are a number of reasons why the above method might not work with a particular endonuclease/methylase system. (1) The two genes may not be closely linked. In that case the two genes cannot be on the same DNA fragment insert. (2) The cloned fragment may, by chance, contain only the methylase gene. A closely linked endonuclease gene might be inactivated by being cut by the restriction enzyme that generated the fragment. Similarly the methylase and endonuclease genes may have been separated from each other by a cut at an intervening restriction site. (3) The level of expression of the endonuclease may be high relative to the expression level of the methylase. In this situation, before the expressed methylase can protect DNA, the expressed endonuclease destroys the vector/insert combination and/or kills the host cell by degrading its chromosome(s). (4) The methylase gene may not be expressed in the new host, leading to lack of protection of DNA from the nuclease. (5) The endonuclease gene may not be expressed in the new host.

Another approach for cloning a restriction enzyme gene is to isolate the protein, obtain an amino acid sequence for at least a portion of it, derive a corresponding nucleic acid sequence, synthesize a nucleic acid probe having the latter sequence, and using that probe to clone the gene. This is far more laborious than the standard method. In situations (1) and (3), if the endonuclease is expressed there will be no methylase enzyme to protect DNA in the host cell and the attempt to clone the endonuclease would fail.

The present invention is based on the hypothesis that the SstI methylase gene would be difficult to express in *E. coli* unless it was on a high copy plasmid and immediately downstream from a strong *E. coli* promoter. This hypothesis was based on the observation that the expression of endonuclease genes in (*E. coli*) from gram positive organisms with a high G +C content (>60%) has often been difficult (SalI: Rodicio and Chater supra, SphI (Guthrie & Meda, U.S. Pat. No. 5,288,696 (1994)), AluI: (Longo et al., U.S. Pat. No. 5,334,526 (1994)), XmaIII, Shandilya, H. S. and Schmidt, B. J., unpublished data). Since we hypothesized that acceptable levels of expression of SstI methylase in the absence of an external *E. coli* promoter was unlikely, the cloning strategy was limited to a design that allowed for expression of the insert by an *E. coli* promoter (the lac promoter) on a high copy vector. Further, a nested deletion approach was used in order to maximize expression of the SstI methylase gene. This is the first time such an approach has been used to express methylase genes when cloning restriction enzymes.

In addition, a selection step in which transformation by plasmids linearized by SstI would generate colonies with the selected phenotype was avoided. Accordingly, a cloning vector was specifically designed to clone the SstI methylase. This vector contained the pMB9 origin of replication and lac promoter found on many common cloning vectors, including pUC19 and pBluescript. In addition, however, this plasmid contained a kanamycin resistance determinant which was flanked by SstI sites. Digestion of unprotected plasmids would not lead to a high background of false kanamycin resistant clones because the kanamycin resistance determinant would be unlinked from the replication origin.

The SstI methylase was cloned by methylase selection (the "Hungarian Trick"), and then the orientation of the methylase gene was determined, and extraneous DNA was deleted to maximize methylase expression. A new library was made and screened for the endonuclease gene with the appropriate probe. One of the *E. coli* strains so identified harbored a plasmid which encoded the SstI endonuclease gene, and produced SstI endonuclease.

The chromosome of the SacI producing organism, *Streptomyces achromogenes* ATCC12767, was examined by hybridization and found to be indistinguishable from the *S. stanford* ATCC29415 chromosome at the SstI/SacI locus.

The overall strategy for reproducing this invention is as follows. DNA is isolated from a SstI producing strain of *Streptomyces stanford*, exemplified herein with ATCC29415 which is on deposit with the American Type Culture Collection, 12301 Parklawn Drive, Rockville, Md. 20852. A recombinant DNA library is made and transformed into a host, preferably *E. coli*, and bulk insert/vector DNA combinations are isolated. Note that the vector must have at least one SstI site which the methylase may protect during the in vitro SstI enzymatic digestion selection step. A portion of this DNA library is then digested with SstI, and the resulting mixture is then transformed into fresh host cells. Clones are picked and DNA from these clones are screened for resistance to digestion by SstI. Clones having DNA that is not degraded by the endonuclease but retain the SstI sites harbor insert/vector combinations carrying the SstI methylase. The extraneous DNA in the insert is trimmed away to establish the location of the methylase gene. A restriction map of the insert and the corresponding region of the chromosome of *S. stanford* is generated. The orientation of the methylase gene in the insert can be determined by subcloning the insert into vectors which have a known promoter adjacent to the insert site, and oriented such that it promotes transcription of the gene in the insert. The orientation of the methylase is deduced from the comparison of the methylase activity in a strain in which the cloned insert is in one orientation with respect to the vector promoter, as opposed to the opposite orientation. The methylase gene is assumed to be in the same direction as the vector promoter in the clone in which methylase activity is higher.

Figure 2A:
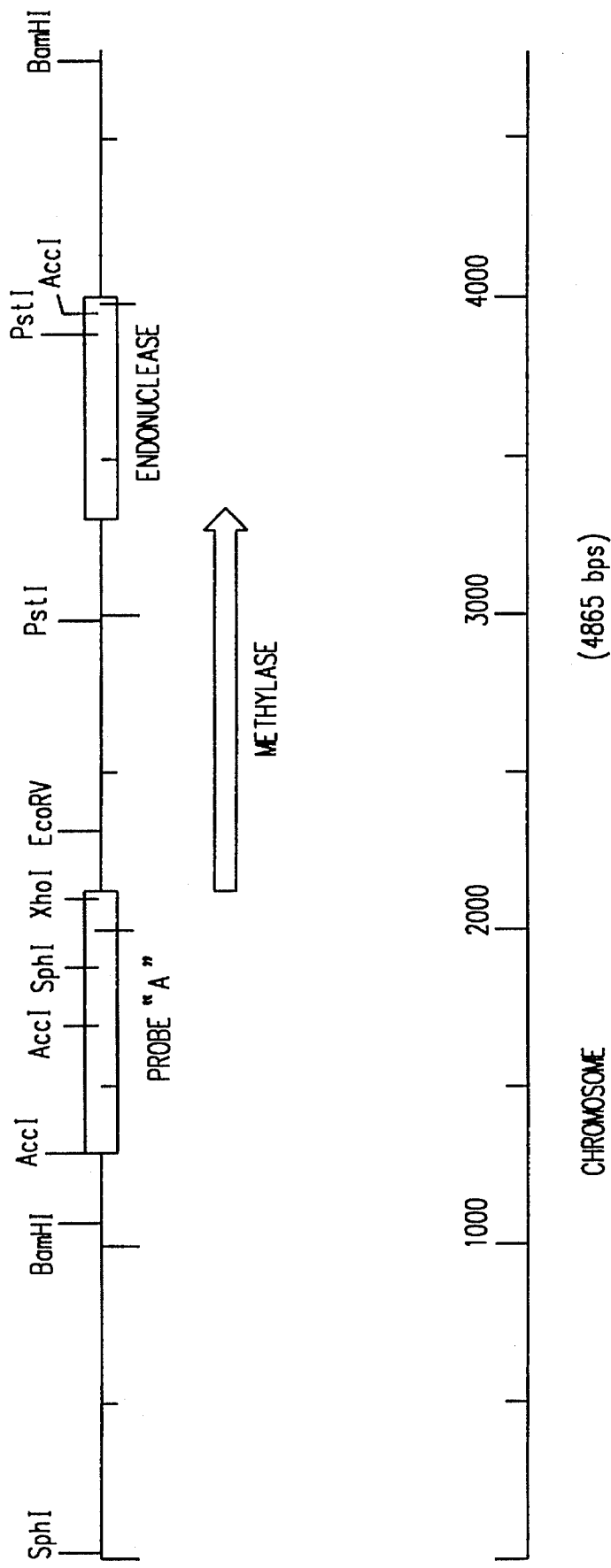
FIGS. 2a, 2b, 2c, 2d, 2e, 2f, 2g, 2h, 2i, 2j and 2k present restriction maps of S. stanford (and S. achromogenes) DNA in the region of the SstI restriction-modification system (FIG. 2a) and the SstI methylase and methylase-endonuclease clones derived from this region (in the case of S. chromogenes, the name "SacI" would be used to describe the locus) (FIGS. 2b to 2k). Not all restriction sites are marked. DNA from the S. stanford genome are shown as double lines. SstI methylase (SstIM) and SstI endonuclease (SstIR) are shown as well as the genes described in FIG. 1. pSst11 (FIG. 2b): the initial SstI methylase clone selected by the "Hungarian Trick"; pSst18 (FIG. 2c): the insert from pSst11 subcloned into pUC18; pSst19 (FIG. 2d): the insert from pSst11 subcloned into pUC19; pSstGEM (FIG. 2e): the insert from pSst11 subcloned into pGEM-7Zf; pSstDEL (FIG. 2f): a deletion derivative of pSstGEM; pSst12 (FIG. 2g): the insert from pSstGEM cloned in front of the RPSL promoter in pSU50; pSst16 (FIG. 2h): the 3.1 kb SphI-BamHI fragment containing the SstI methylase and endonuclease genes cloned in pUC19; pSst33 (FIG. 2i): the insert from pSst16 cloned into pTTQ19; pSst53 (FIG. 2j): deletion derivative of pSst33 in which sequences clockwise from the BamHI site have been deleted; pSst105 (FIG. 2k): deletion derivative of pSst53 in which sequences counterclockwise from the tac promoter have been deleted. A non-radioactive probe ("A") was generated from pSstGEM by cleaving with XhoI/AccI and isolating the approximately 400 base pair fragments.
Figure 2C:
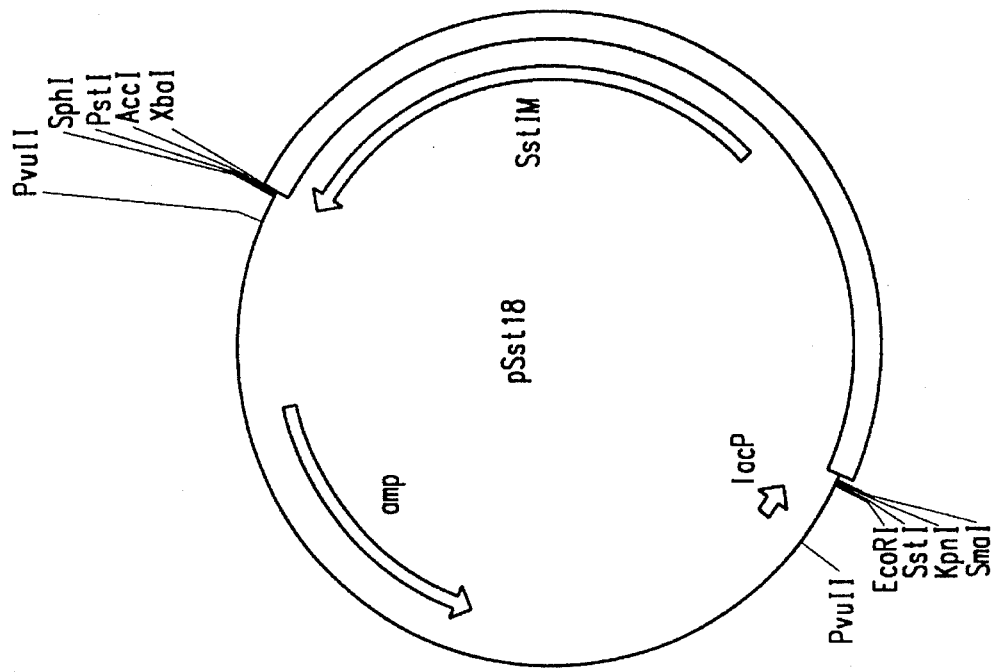
Figure 2B:
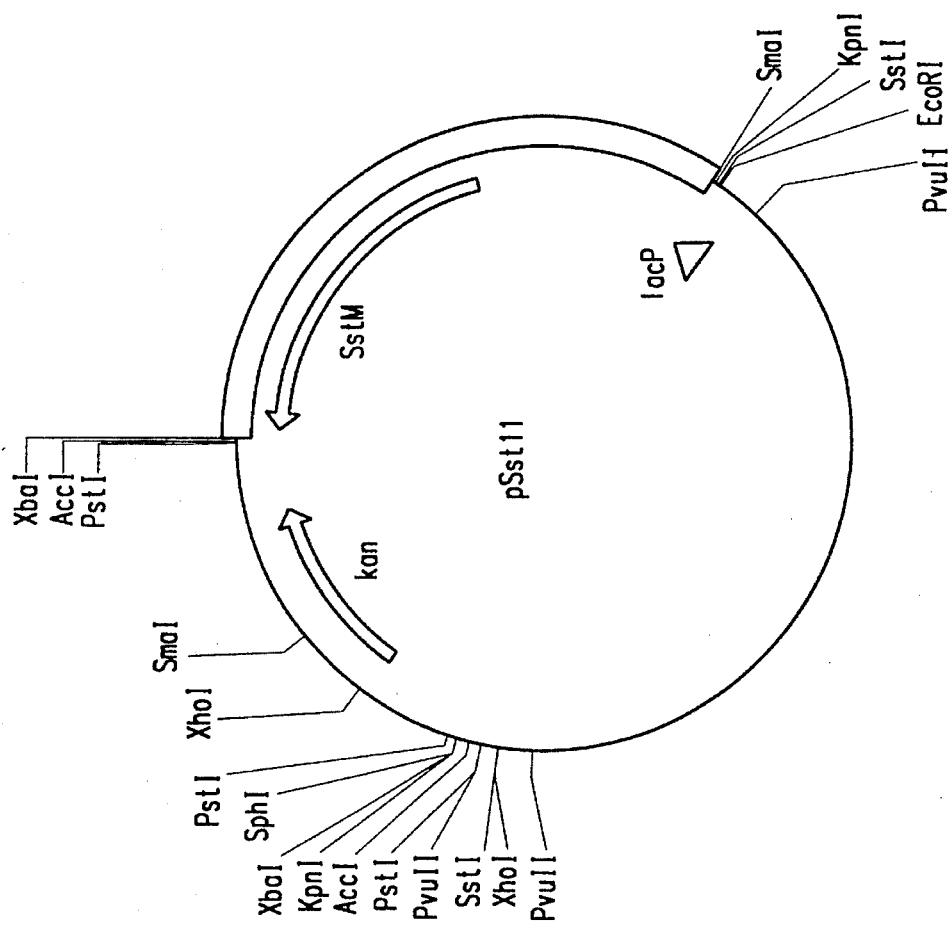
Figure 2E:
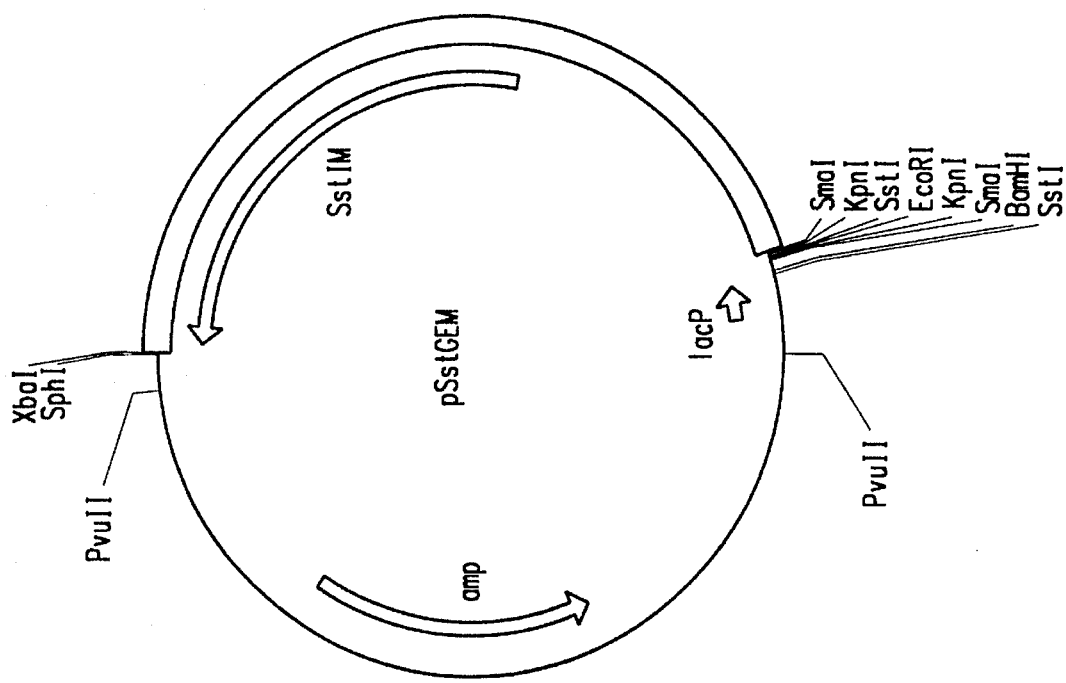
Figure 2D:
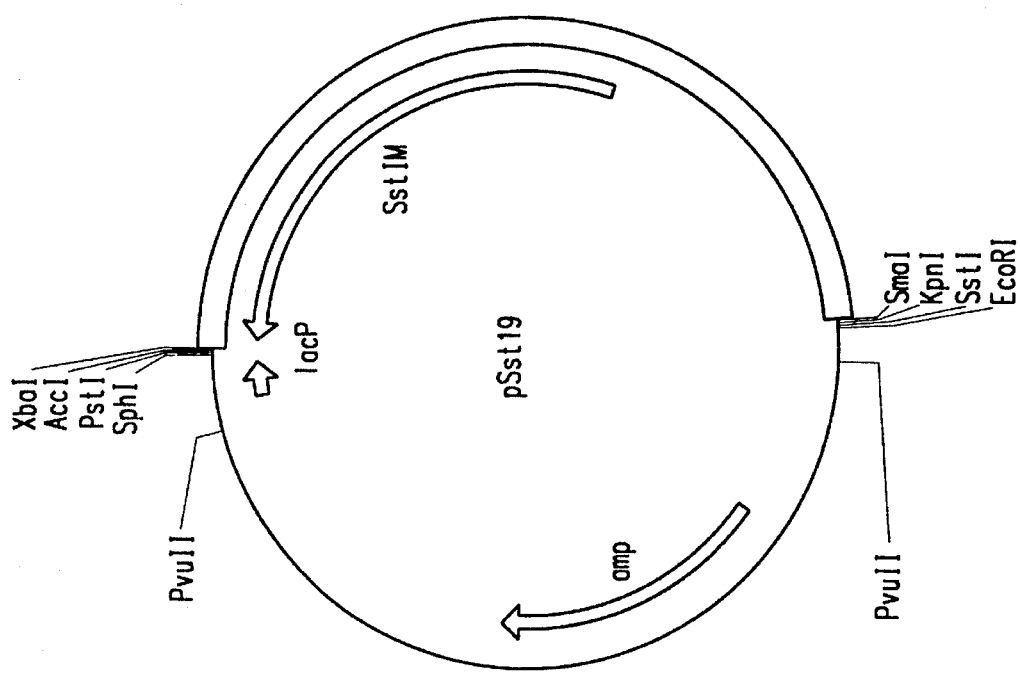
Figure 2G:
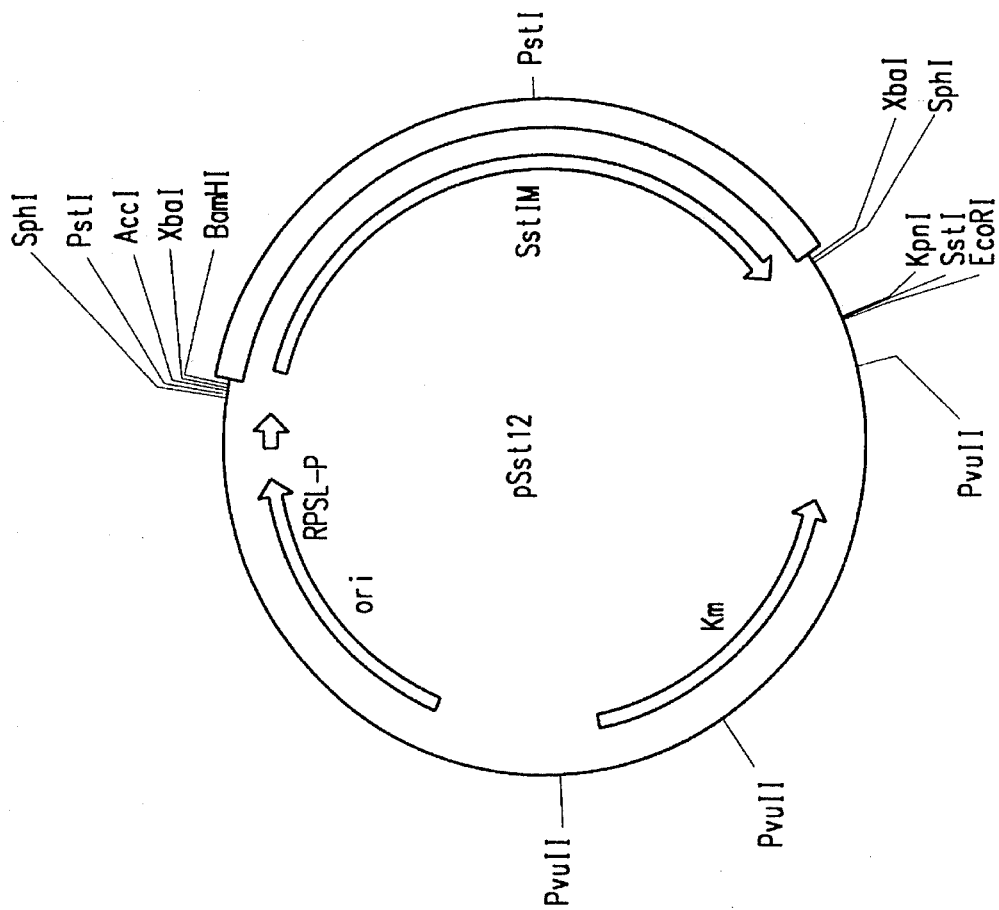
Figure 2F:
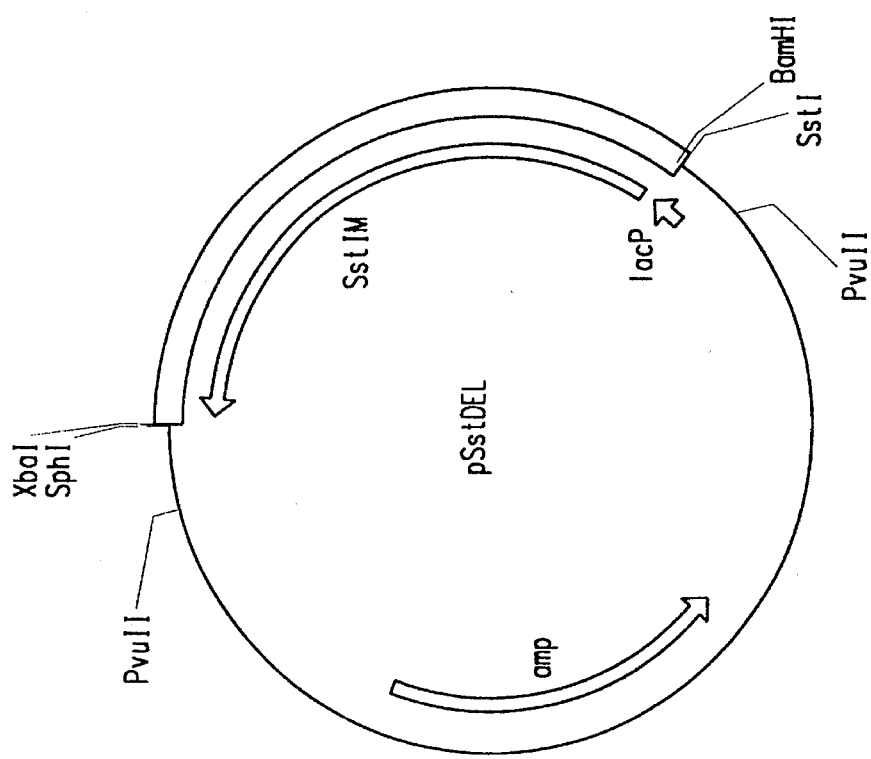
Figure 2H:
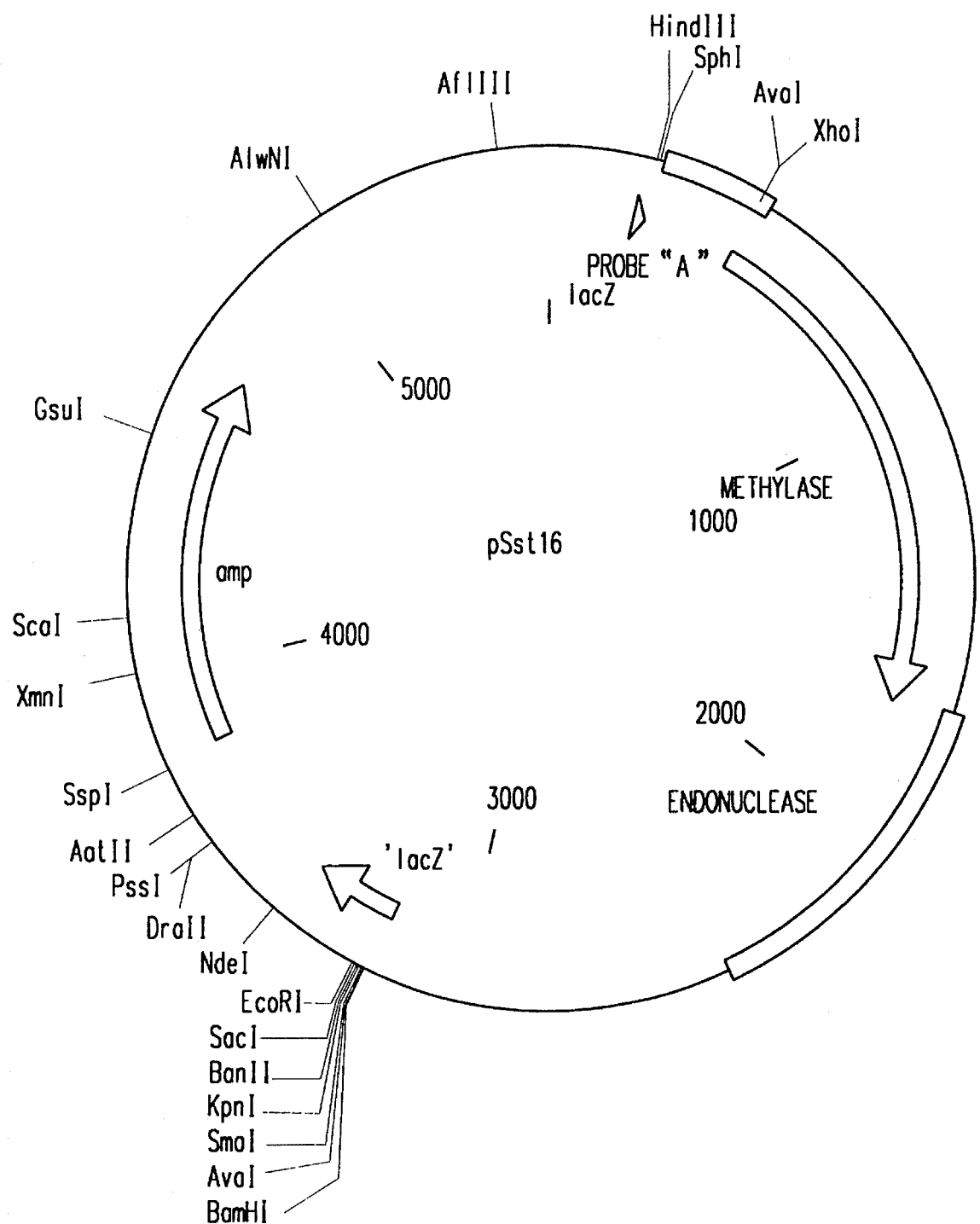
Figure 2J:
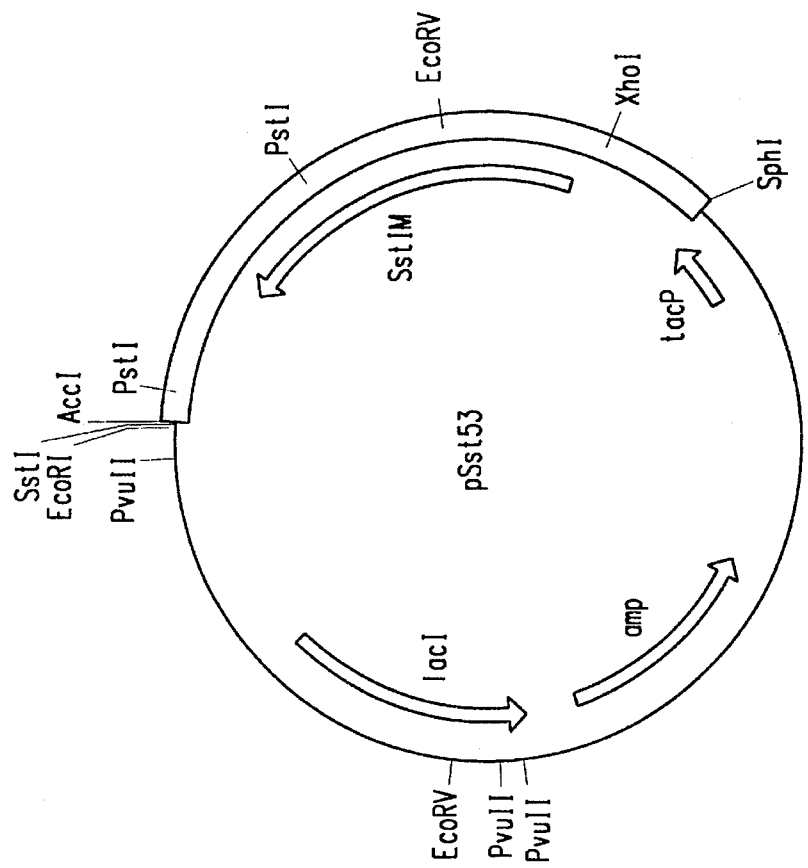
Figure 2I:
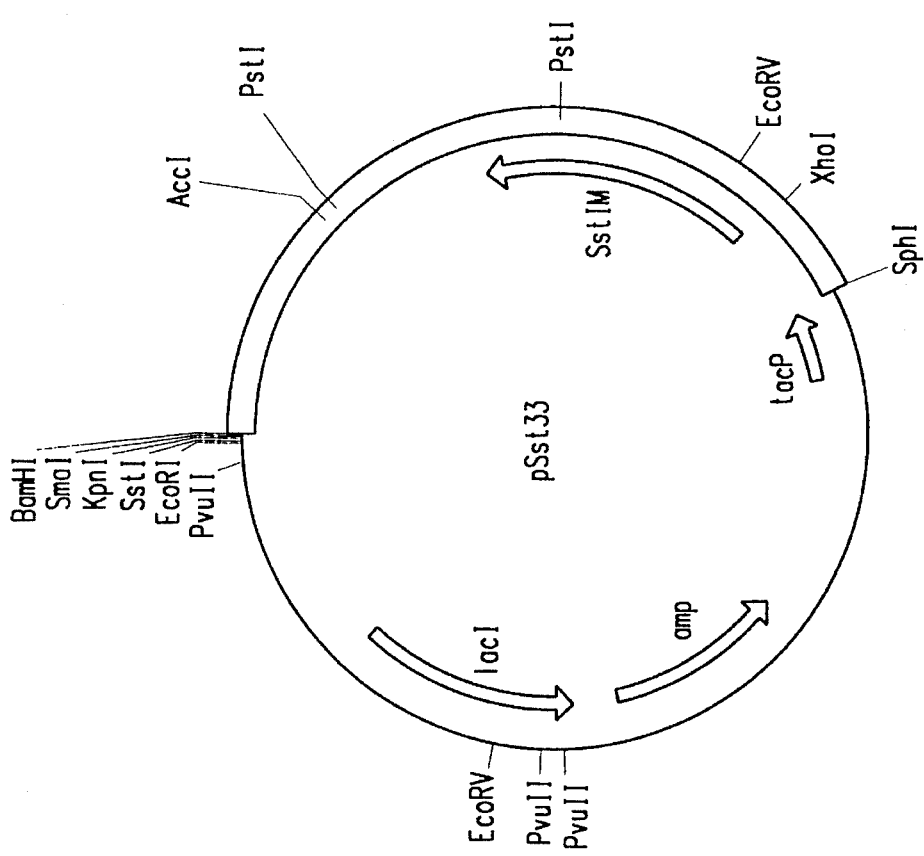
Figure 2K:
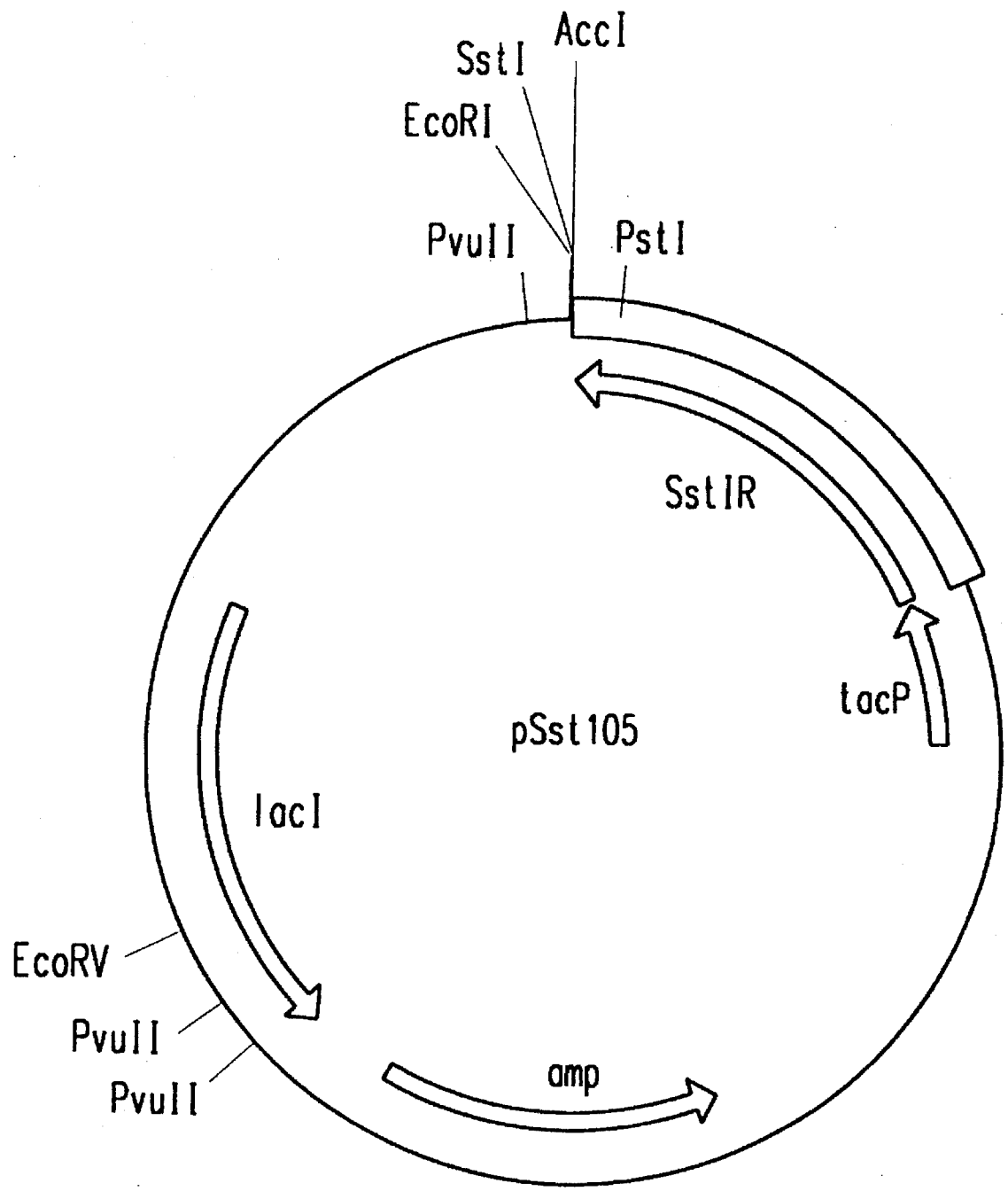

The resulting clones express SstI methylase but not SstI endonuclease. New libraries are made with complete digests by restriction enzymes which create fragments in which DNA extending downstream from the methylase gene are cloned in such a way as to place a strong promoter directly upstream from the methylase gene. These libraries are screened by hybridization. Probes which may be used are those which correspond to the sequence in the XhoI/AccI fragments of pSstGEM which are not present in pSst12 (FIG. 2). Cells harboring these clones are then screened for appropriate restriction sites in the insert. Clones with the anticipated sites are chosen.

The present invention further encompasses the expression of the desired restriction endonuclease and modification methylase in prokaryotic and eukaryotic cells. Eukaryotic and prokaryotic hosts that may be used for cloning and expressing the enzymes of the invention are well known in the art. Vectors which replicate in such host cells are also well known (Maniatis et al., *Molecular Cloning: A Laboratory Manual*, Cold Spring Harbor Laboratory Press, Cold Spring Harbor, N.Y. (1982)).

Preferred prokaryotic hosts include, but are not limited to, bacteria of the genus Escherichia, Bacillus, Streptomyces, Pseudomonas, Salmonella, Serratia, Caryophanon, etc. The most preferred prokaryotic host is *E. coli*. Bacterial hosts of particular interest in the present invention include *E. coli* K12 and DH10B.

It has been found that *E. coli* has several mechanisms (restriction systems) for identifying foreign DNA and destroying it. This can be a significant problem in cloning experiments, resulting in reduced recovery of the desired sequences. In particular, it has been found that *E. coli* contains restriction systems that degrade DNA when it is methylated, either on cytosine residues or adenine residues. Specifically, the well known methylcytosine-specific systems include mcrA (rglA), and mcrB (rglB) (Revel et al., Virology 31:688–701 (1967); Raleigh et al., *Proc. Natl. Acad. Sci. USA* 83:9070–9074 (1986)). The methyladenine-specific restriction system has been designated mrr (Heitman et al., *J. Bacteriol.* 169:3243–3250 (1987)). Thus, the preferred host for cloning and expressing the genes encoding for the enzymes of the present invention are hosts in which these types of restriction systems have been inactivated through mutation or loss.

Once the desired restriction endonuclease and modification genes have been isolated, a number of recombinant DNA strategies exist for enhanced production of the desired protein in eukaryotic or prokaryotic hosts. These strategies, which will be appreciated by those skilled in the art, utilize high copy number cloning vectors, expression vectors, inducible high copy number vectors, etc.

Enhanced production of the restriction endonuclease and modification methylase can be accomplished, for example, by operably linking the desired gene to a strong prokaryotic promoter, although the natural restriction or modification methylase gene promoter may be used. Such well known promoters may be either constitutive or inducible. Examples of constitutive promoters include the int promoter of bacteriophage λ, and the bla promoter of the β-lactamase gene of pBR322, etc. Examples of inducible prokaryotic promoters include the major left and right promoters of bacteriophage λ($P_L$ and $P_R$), the trp, recA, lacZ, gal, tet, trc, and tac promoters of E. coli, the α-amylase (Ulmanen, I., et al., J. Bacteriol. 162:176–182 (1985)), the $\delta^{28}$– specific promoters of B. subtills (Gilman, M. Z., et al., Gene 32:11–20 (1984)), the promoters of the bacteriophages of Bacillus (Gryczan, T. J., In: The Molecular Biology of the Bacilli, Academic Press, Inc., N.Y. (1982)), and Streptomyces promoters (Ward, J. M., et al., Mol. Gert. Genet. 203:468–478 (1986)). Prokaryotic promoters are reviewed by Glick, B. R., (J. Ind. Microbiol. 1:277–282 (1987)); Cenatiempo, Y. (Biochimie 68:505–516 (1986)); and Gottesman, S. (Ann. Rev. Genet. 18:415–442 (1984)).

A strong promoter can be chosen by searching for a promoter that has a sequence closely resembling that of the consensus sequence for the host. Consensus E. coli promoters are well known in the art (Rosenberg, M. and Court, D. (1979) Ann. rev. Genet. 13:319–353; Lisser, S. and Margalit, H. (1993) Nucleic Acids Res. 21: 1507–1516).

One preferred strong promoter is the rps 1 (ribosomal protein small subunit 1) promoter (Post, L. E. et al. (1978) Cell 15:215–229) (also known as "Str" streptomycin resistance promoter).

In order to enhance the production of the desired restriction endonuclease in a prokaryotic cell, it is important to achieve a level of expression of the corresponding modification methylase gene sufficient to protect the DNA of the recombinant host against cleavage with the cloned restriction endonuclease. Therefore, it may be necessary to enhance the level of methylase expression when expressing the endonuclease.

Furthermore, those skilled in the art will recognize that various ways of maintaining both the modification and restriction genes within the same recombinant host can be employed, e.g. the genes may be on the same or separate vectors. The only requirement, when cloning restriction endonuclease genes, is that the recombinant host contain and express the methylase gene corresponding to the endonuclease gene being cloned.

The clones described herein may be improved by sequencing the endonuclease and methylase genes and subcloning each gene in front of suitable promoters with the ribosome binding sites placed in the correct position. The procedures for doing this are well known to those of ordinary skill in the art. In particular, the endonuclease may be under better control when amplified by PCR using an oligonucleotide which changed the sequence at the amino terminal start site to 5' CAT ATG 3', where ATG is the start codon, and then subcloned into the NdeI site of a vector such as pRE1 and pRE2 (Reddy et al. (1989) Nucl. Acids Res. 24:10473–10488). This optimizes expression and controls leaky expression at the same time. Other improvements could also be made, such as cloning the endonuclease gene in front of the T7 or other promoters, or cloning the endonuclease gene on a runaway replication plasmid (Hammond, A. W. et al. (1990) Gene 97:97–102).

The enzymes of this invention, SstI/SacI and SstI/SacI methylase, or isoschizomers thereof, are preferably produced by fermentation of the recombinant host (prokaryotic or eukaryotic) containing and expressing the cloned restriction endonuclease and/or modification methylase genes. The recombinant host, such as E. coli, producing the cloned proteins, can be grown and harvested according to techniques well known in the art.

After culturing, the recombinant host cells of this invention can be separated from the culture liquid, for example, by centrifugation. The modification methylase and/or restriction enzymes produced by this host can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, desired enzyme can be purified by extraction, ion-exchange chromatography, molecular-sieve chromatography, affinity chromatography, and the like, giving the restriction endonuclease of this invention.

According to the present invention, assays to detect the presence of the restriction endonucleases and modification methylases can be used during the conventional biochemical purification methods to determine the presence of these enzymes.

The restriction endonuclease can be identified on the basis of the cleavage of its recognition sequence. For example, lambda (λ) DNA can be used as a substrate. After digestion with endonuclease, the DNA fragments are separated electrophoretically in agarose gels in the buffer systems conventional for fragment separation and in the presence of ethidium bromide (EtBr).

Demonstration of modification methylase activity can be, but is not limited to, a two-step identification process. First, substrate DNA (λ DNA) that contains the recognition sequence is incubated with column fractions to be tested for methylase activity. Second, this DNA is then challenged with the corresponding restriction activity to identify those fractions which contain methylase activity. For example, while assaying for SstI methylase, the DNA samples will be challenged with SstI. Thus, DNA samples which do not exhibit cleavage with SstI contain SstI methylase activity.

Having now generally described the invention, the same will be more readily understood through reference to the following Examples which are provided by Way of illustration, and are not intended to be limiting of the present invention, unless specified.

EXAMPLES

Example 1

Experimental 1.1: Definition of abbreviations

Ad-2, adenovirus-2; Ap, ampicillin; bp, base pair(s); EtBr, ethidium bromide; kbp, 1000 base pairs (bp); IPTG, isopropylthio-beta-galactoside; Km, kanamycin; PolIK, Klenow (large) fragment of E. coli DNA polymerase I; PCR, polymerase chain reaction; [R], resistance; [S], sensitivity; SDS, sodium dodecyl sulfate; Sp, spectinomycin; Tc, tetracycline; and X-Gal, 5-bromo-4-chloro-3-indolyl-beta-D-galactoside.

1.2: Bacterial Strains and Growth Conditions

Streptomyces strains were grown at 28° C. to mid-log phase in trypticase soy broth. *Streptomyces stanford* strain ATCC 29415 makes SstI (Goff & Rambach, *Gene* 3:347–352 (1978)) and SstII. *Streptomyces achromogenes* strain ATCC12767 was obtained from the ATCC and makes restriction enzymes SacI (Zhuraulera L. I. et al., *Prikl. Biokhim. Mikrobiol.* 23(2):208215 (1987)) and SacII.

*E. coli* strains were grown at 37° C. in YET broth (5 g/l yeast extract, 10 g/l tryptone, and 5 g/l NaCl) or Circlegrow (Bio101) with antibiotic supplements of 100 mg/l ampicillin; 20 mg/l chloramphenicol; and 50 mg/l kanamycin; as appropriate. *E. coli* strain DH10B and DH10BRec+ were used for cloning the SstI genes. DH10B is a recA1$^-$, endA$^-$, phi80dlacZdeltaM15 derivative of MC1061 (Casadaban & Cohen, *J. Mol. Biol.* 138:179–207 (1980)). DH10BRec+ is a derivative of DH10B which has a wild-type RecA allele. Competent *E. coli* strains were either obtained from BRL or made by a protocol described by Hanahan, D, *J. Mol. Biol.* 166:557–580 (1983).

1.3: Vectors/Plasmids

Because a methylase protection scheme was to be used to clone SstI restriction and modification genes, it was necessary to use vectors containing SstI site(s). The plasmids pUC-4K and pSL1180 are from Pharmacia LKB Biotechnology, 800 Centennial Avenue, Piscataway, N.J. 08854.

pSLKS101 was created by the following method. The 1.3 kb PstI fragment from pUC4-K into the PstI site of pUC19, forming pUCKT. The 1.3 kb EcoRI-SphI fragment of pUCKT was subcloned into the EcoRI-SphI sites of pSL1180, forming pSLKS102. pSU50 is a subclone of pSU39 (Bartolome B. et al., Cruz, *Gene* 102:75–78 (1991)), in which the lac promoter has been replaced by the rpsl promoter of *E. coli*. pTTQ18 and pTTQ19 are expression vectors in which the tac promoter is immediately upstream from a multiple cloning site (Stark, M. J. R., *Gene* 51:255–267 (1987)). The sequence of sites in the multiple cloning site in pTTQ18 is the inverse of that in pTTQ19.

1.4: DNA Isolations

Small scale plasmid DNA isolations were performed by an alkaline lysis method (Maniatis Tet at., *Molecular Cloning, a laboratory manual*, Cold Spring Harbor Laboratory, Cold Spring Harbor, N.Y. (1982)). For large scale plasmids preparations, the alkaline procedure was followed by EtBr-CsCl density gradient centrifugation as described in Maniatis supra.

*S. stanford* ATCC29415 total genomic DNA was isolated by grinding frozen cells with cold 100 mesh glass beads to a fine powder, resuspending in 10 ml of SNET buffer (2% sarkosyl, 50 mM Tris•HCl, pH 8.0, 50 mM NaCl, and 50 mM EDTA (ethylene diamine tetraacetic acid). After cell lysis, the lysate centrifuged (4,000 rpm 40 min) and the supernatant was treated with 100 μg/ml RNase at 50° C. for 30 min. Proteinase K was added to 50 μg/ml and the mixture incubated for 30 minutes at 37° C. The mixture was extracted once with phenol and once with chloroform. The DNA was further purified by CsCl gradient centrifugation and the DNA-containing fractions were pooled and dialyzed against TE. The DNA was precipitated with ethanol, and the precipitate spooled on a glass rod, washed in 70% ethanol, and resuspended in TE.

DNA fragments to be cloned were usually isolated by the gene-clean procedure (Bio 101).

1.5: Colony and Southern Hybridization

Hybridizations were performed using biotinylated probe and photo-gene detection using the PhotoGene Nucleic Acid Detection System (LTI). Fragments generated by endonuclease digestion of the appropriate plasmid were separated by agarose gel electrophoresis and isolated from agarose gel slices by the Gene-Clean procedure (Bio101 Inc, P.O. Box 2284, La Jolla, Calif. 92038–2284). Fragments were then labeled with biotin by octamer-primed synthesis in the presence of biotinylated nucleotides using the BioPrime DNA Labeling System (LTI).

1.6: Construction of Genomic Libraries

A library of *S. stanford* ATCC29415 genomic DNA was constructed in pSLKS101. pSLKS101 DNA was digested with BamHI and dephosphorylated using calf intestine alkaline phosphatase (LTI). Genomic DNA of ATCC29415 was digested partially with Sau3AI and 2–4 kb fragments were isolated by velocity sedimentation in a NaCl gradient. 100 ng of pSLKS101 vector DNA was ligated with 800 ng of fractionated chromosomal DNA using 2 units of T4 DNA ligase in 1×ligase buffer (BRL) overnight at room temperature. The ligated DNA was transformed into DH10B by electroporation. A small amount of the transformation mix was diluted and plated on kanamycin-LB agar to determine the total number of transformants (approximately 62,000 Km$^R$ transformants). The remainder of the transformation mix was inoculated into 200 ml of LB media (LTI) containing kanamycin. After 16 h of growth at 30°, the cells were harvested and plasmid DNA (large scale) was purified as described above.

1.7: Assay for Restriction Enzyme

Overnight cultures (20 ml) were harvested and resuspended in 1 ml buffer containing 10 mM Tris•HCl (pH 7.5), 10 mM beta-mercaptoethanol and 1 mM EDTA. Cells were sonicated on ice by three 10 second blasts with a micro-tip probe. A portion of the crude extract was added to AD2 DNA in 1×BRL REact™2 buffer and incubated for 1 hour at 37° C. DNA was fractionated by electrophoresis and visualized by EtBr staining.

1.8: Generation of a nested set of deletion derivatives

A set of deletions of an insert can be obtained by timed exonuclease digestion if the plasmid is linearized at one junction between the vector and the insert with an appropriate combination of two enzymes (Henikoff, Gene 28:351 (1984)). Plasmid DNA was cleaved with two enzymes and the digest was treated with phenol-chloroform and precipitated with ethanol. The DNA precipitate was resuspended in an appropriate volume of TE and subjected to degradation by ExonucleaseIII. At timed intervals, aliquots were removed from the exonuclease digestions, the exonuclease action was halted, the ends of the DNA polished with S1 nuclease and Polk polymerase, the DNA fragments self-ligated in a mixture containing T4 DNA ligase buffer (LTI) and T4 DNA ligase (LTI). The ligation mixture was used to transform DH10B/pSst12 recipients, and individual transformants were analyzed. pSstGEM was cleaved with EcoRI/KpnI, pSst33 was cleaved with BamHI/KpnI, and pSst53 was cleaved with SphI/XhoI.

1.9: Buffer compositions

TE: 20 mM Tris, 1 mM EDTA, pH 8.0. Phenol-chloroform: 1:1 mixture of phenol and chloroform.

Example 2

Selection of Clones Expressing Methylase and Endonuclease

Clones expressing SstI methylase were selected by digesting 14μg of the library DNA overnight with more than 100 units of SstI. The digested DNA was dephosphorylated, extracted with phenol, and ethanol precipitated. A portion of the digested DNA was used to transform *E. coli* DH10B cells, and kanamycin-resistant transformants were selected. Plasmid DNA from 24 clones was tested for resistance to SstI. Protection of the resident plasmid and the host chromosomal DNA from digestion with SstI indicated the presence of methylase activity. Eight transformants were selected which were partially protected from SstI digestion.

Example 3

Identification of Methylase Clones

Plasmid DNA was from $Km^R$ clones surviving the SstI selection procedure on the pSLKS102 library were subjected to further analysis. The clones apparently fell into two groups: those with 2.5 kb inserts (six isolates), and those with 5.5 kb inserts (two isolates). It was reasoned that since the inserts were size-selected (2 to 4 kb), the 5.5 kb inserts were likely to have arisen from a double insertion event in a single vector, and these two clones were put aside. The other six clones with 2.5 kb inserts were apparently sister clones and one was chosen for further study (pSst11).

Example 4

Subcloning of the SstI Methylase Gene

Determining the orientation of the SstI methylase gene

The 2.5 kb insert in pSst11 was removed by digesting with EcoRI+XbaI and cloned into the EcoRI-XbaI sites in pUC18 (forming pSst18), pUC19 (forming pSst19) and pGEM-7Zf(forming pSstGEM). Since pSst18 and pSstGEM were largely protected from SstI digestion and pSst19 was not, it was deduced that the amino end of the SstI methylase gene was toward the EcoRI site, and the carboxy end of the SstI methylase gene was toward the XbaI site, such that the lac promoter in pUC18 (or pSstGEM) was largely responsible for the SstI methylase expression.

Determining the limits of the SstI methylase gene

Having determined the orientation of the SstI methylase gene, the approximate location of the beginning of the gene was determined by making a nested set of deletions at the EcoRI end of the insert in pSstGEM, and characterizing the largest deletion that still retained SstI methylase activity. A clone with an insert of about 1.5 kb was isolated (pSstMdel). Since this insert was sufficiently small, a 1600 bp BamHI/PvuII fragment of pSstMdel was subcloned into the BamHI/SmaI site of pSU50, forming pSst12. In pSst12, the SstI methylase gene is oriented such that SstI methylase expression is under the control of the strong rps 1 promoter.

Example 5

Chromosomal Localization the SstI Methylase Gene

The *S. stanford* genome contiguous to the SstI methylase gene was mapped to identify which restriction sites were present at the locus. Southern blot analysis of *S. stanford* ATCC29415 chromosomal DNA digested with various restriction enzymes led to the construction of the map of the *S. stanford* chromosome in the region of the SstI methylase gene (FIG. 2).

Example 6

Cloning of the SstI Endonuclease Gene in a Protected Host

On the basis of the map of the SstI region, the 3.1 kb BamHI/SphI fragment containing the SstI endonuclease gene was cloned as follows. *S. stanford* ATCC29415 DNA was cleaved with BamHI and SphI, the digest was electrophoresed in an agarose gel, the fragments between 2.7 and 4 kb were excised, isolated from the gel slice by the Gene-Clean procedure and ligated with BamHI/SphI-cleaved pUC19 DNA. The ligation mixture was used to transform DH10BRec+/pSst12 recipient cells. This small library was screened by colony hybridization, using the XhoI-AccI probe shown in FIG. 2. Colonies which gave a positive hybridization signal were analyzed with restriction enzymes. Only one clone had a restriction pattern which matched that expected on the basis of the *S. stanford* chromosomal map, and was chosen for further study (pSst16).

Example 7

Subcloning the SstI Endonuclease gene for increased expression

The 3.1 kb BamHI/SphI insert in pSst16 was subcloned into pTTQ18 and pTTQ19, thus placing the same insert in both orientations with respect to the tac promoter. SstI endonuclease activity was detected in pSst33 (a pTTQ19 derivative) but lower amounts were detected in pSst48 (a pTTQ18 derivative). Therefore it appeared that the SstI endonuclease gene was in the same orientation as the methylase gene, (from SphI to BamHI). A nested set of deletions was generated at the BamHI end of the insert in pSst33. In one deletion clone (pSst53), about 880 bp of the insert had been deleted without affecting SstI endonuclease expression. A nested set of deletions of pSst53 was generated, this time from the other end of the insert (the SphI side). One clone arising from this experiment, pSst105, was found to generate over 400,000 units of SstI per gram of cells, a significant improvement over the previous clones.

Example 8

Analysis of the SacI locus in S. achromogenes

Figure 1B:
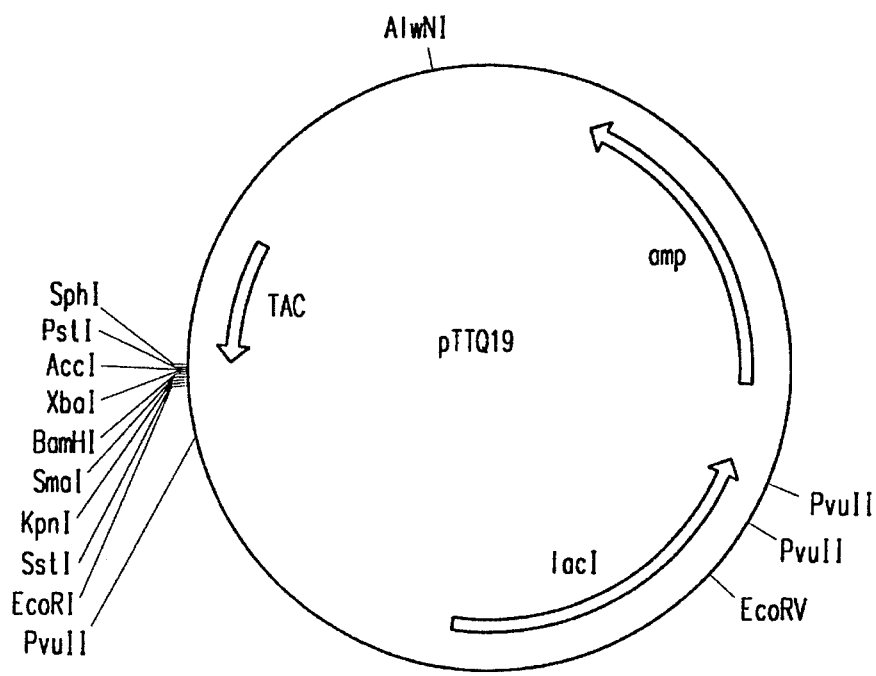
Figure 1D:
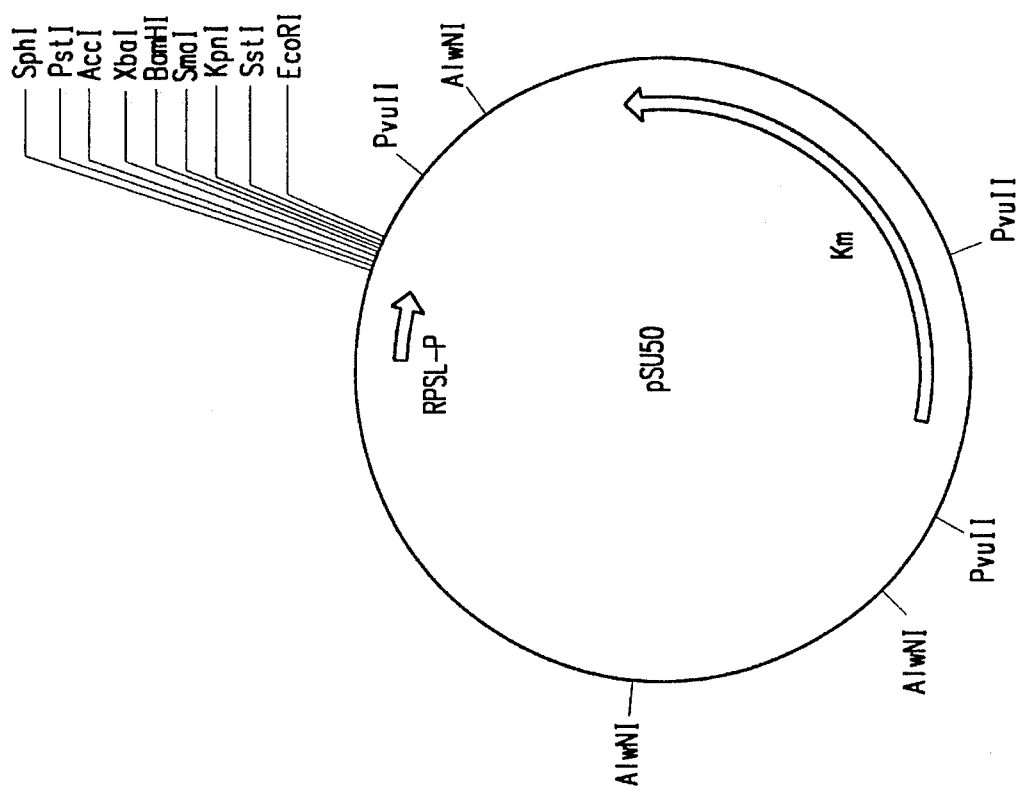
Figure 1C:
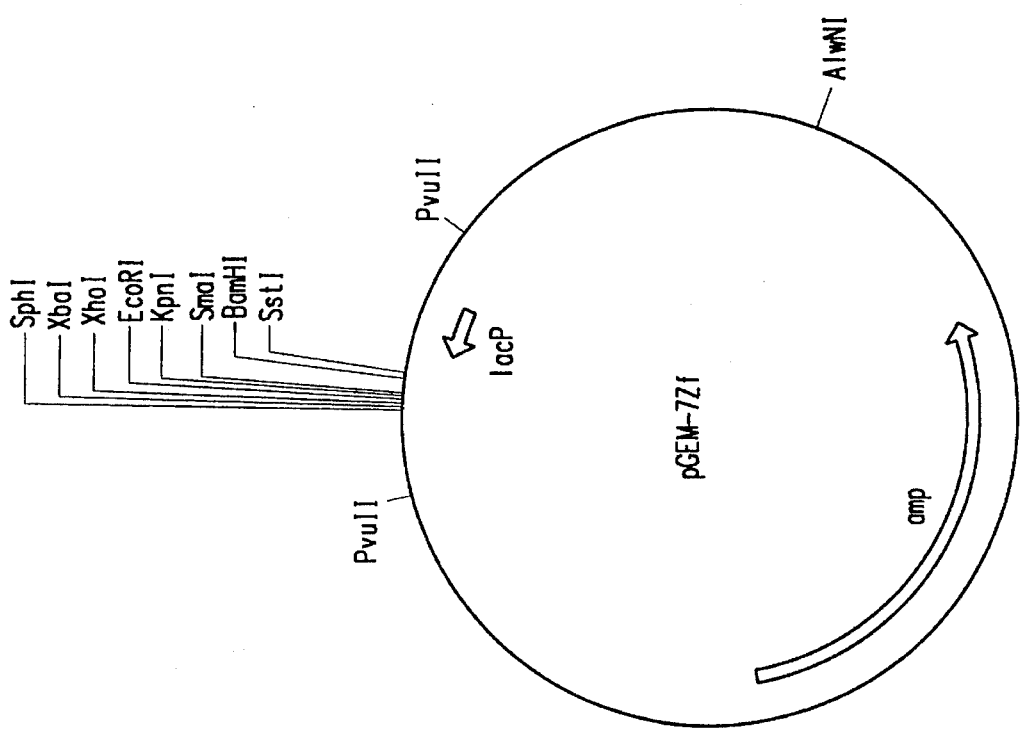
Figure 1E:
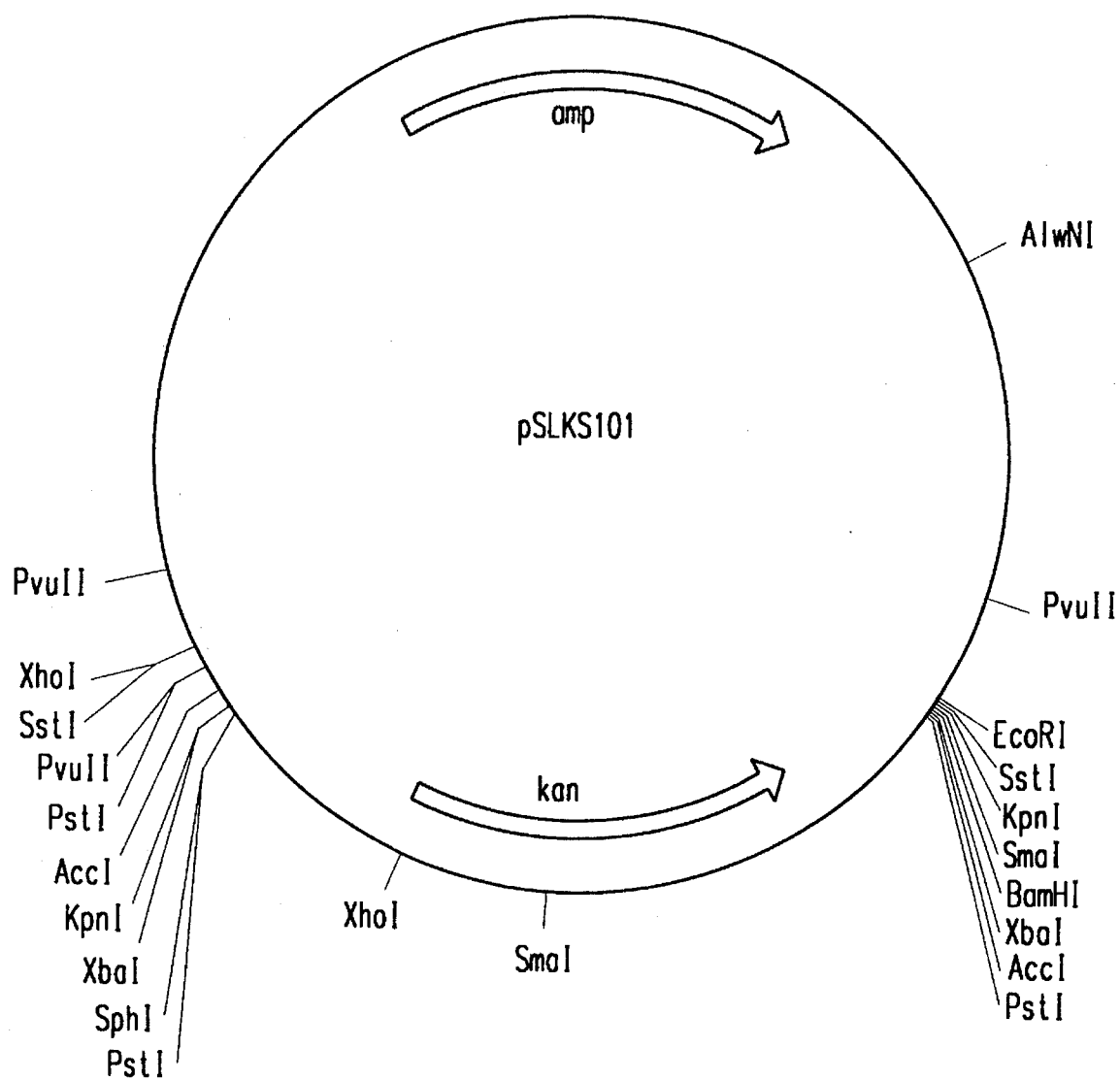

*S. achromogenes* ATCC12767 genomic DNA was isolated, digested with restriction endonucleases singly and in combination (SphI, SphI/BamHI, BamHI, AccI, SphI/EcoRV, XhoI/SatI, PstI/SphI, PstI, XhoI/AccI), and electrophoresed in an agarose gel. The overall pattern of the digests was indistinguishable from the corresponding patterns obtained with *S. stanford* genomic DNA. The S. achromogenes digests were blotted and probed with probe "A" (FIG. 1). The resulting hybridization pattern was identical to that obtained with the same probe on similarly treated *S. stanford* genomic DNA.

These data may be used by those of ordinary skill in the art to clone the SstI genes from *S. stanford* ATCC29415 or the SacI genes from *S. achromogenes* ATCC12767 or similar genes from similar bacteria and express them in a heterologous host. The SstI (or equivalent) methylase gene may be cloned without a complete, functional endonuclease gene from the genomic DNA or from pSst12 by any of several combinations of restriction endonucleases. The data provided in FIG. 2 can be used by those of ordinary skill in the art to clone the SstI (or equivalent) endonuclease gene using well known methods of molecular biology and genetic engineering.

Example 9

Increasing the Level of Methylase

Two microliters of a ligation mix of chromosomal DNA (0.0225 pmol) isolated as in Example 6, and BamHI/SphI-cleaved pUC19 vector DNA (0.0075 pmol) were co-transformed with about 80 ng of pSst12 DNA into 100 μl of *E. coli* DH10B Rec+ competent cells. The mixture was placed on ice for 25 min followed by a 40 sec 42° C. heat shock. Nine hundred milliliters of SOC medium was added and cells were allowed to express for 1 hr at 30° C. Cells were then plated on X-gal plates having LB medium supplemented with 100μg/ml ampicillin, and 50 μg/ml kanamycin. Colonies (6000–7000) were screened by hybridization as described in Example 6. Of about 20 colonies identified, 12 were tested for the presence of SstI endonuclease; 4 were found to express the endonuclease. Thus in cases where the endonuclease is expressed from the natural promoter pre-protection of the host is not necessary if one increases the level of expression of the methylase.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A recombinant DNA molecule comprising:
   (a) a vector, and
   (b) a structural gene encoding SstI or SacI restriction endonuclease
      wherein the structural gene is linked to the vector,
      whereby the structural gene may be maintained in a cell by the vector.

2. The molecule as in claim 1, further comprising
   (c) a promoter,
      wherein the promoter is linked to the structural gene and the vector,
      whereby the promoter may be maintained in a cell by the vector, and
      wherein the promoter is in such position and orientation with respect to the structural gene that the structural gene may be expressed under control of the promoter,
      whereby the SstI or SacI endonuclease protein encoded by the structural gene may be expressed under control of the promoter.

3. The molecule as in claim 2, wherein the promoter is a SstI or SacI endonuclease gene promoter.

4. The molecule as in claim 1, further comprising
   (d) a SstI or SacI restriction modification methylase gene,
      wherein the methylase gene is linked to the structural gene and the vector,
      whereby the methylase gene may be maintained in a cell by the vector, and
      wherein the methylase gene is capable of protecting DNA contained by a host cell from degradation by SstI or SacI endonuclease.

5. A method of producing a restriction endonuclease comprising, in series, the steps of
   (A) simultaneously transforming a cell with
      (1) a first DNA molecule comprising
         (a) a structural gene encoding a restriction endonuclease
         (b) a promoter,
            wherein the promoter is linked to the structural gene, and
            wherein the promoter is in such position and orientation with respect to the structural gene that the structural gene is expressed under control of the promoter,
            whereby the endonuclease protein encoded by the structural gene is expressed under control of the promoter, and
      (2) a second DNA molecule comprising
         (c) a restriction modification methylase gene,
            wherein the methylase gene is linked to a promoter, and
            wherein the methylase gene is capable of protecting DNA contained by a host cell from degradation by said endonuclease,
   (B) growing said transformed cell, and
   (C) extracting said endonuclease from the cell of step (A), whereby said endonuclease is produced.

6. The method as in claim 5, wherein the restriction endonuclease is a SstI or SacI restriction endonuclease.

7. The method as in claim 5, wherein the methylase gene is a SstI or SacI methylase gene.

8. The method as in claim 5, wherein the promoter linked to the methylase gene is a heterologous promoter.

9. The method as in claim 5, wherein the promoter of the first DNA molecule is a SstI or SacI endonuclease gene promoter.

10. A method as in claim 5, further comprising after step (C) the step of
    (D) purifying said endonuclease.

11. A method of producing a restriction endonuclease comprising, in series, the steps of
    (A) preparing a transformed cell comprising
       (1) a first DNA molecule comprising
          (a) a structural gene encoding a restriction endonuclease
          (b) a promoter,
             wherein the promoter is linked to the structural gene, and
             wherein the promoter is in such position and orientation with respect to the structural gene that the structural gene is expressed under control of the promoter,
             whereby the endonuclease protein encoded by the structural gene is expressed under control of the promoter, and
       (2) a second DNA molecule comprising
          (c) a restriction modification methylase gene,
             wherein the methylase gene is operably linked to a heterologous promoter, and
             wherein the methylase gene is capable of protecting DNA contained by a host cell from degradation by said endonuclease,
    (B) growing said transformed cell, and
    (C) extracting said endonuclease from the cell of step (A), whereby said endonuclease is produced.

12. The method as in claim 11, wherein the restriction endonuclease is a SstI or SacI restriction endonuclease.

13. The method as in claim 11, wherein the methylase gene is a SstI or SacI methylase gene.

14. The method as in claim 11, wherein the promoter of the first DNA molecule is a SstI or SacI endonuclease gene promoter.

15. The method as in claim 11, wherein the promoter of the second DNA molecule is a strong promoter.

16. A method as in claim 11, further comprising after step (C) the step of
   (D) purifying said endonuclease.

17. A cell, wherein the cell contains a SstI or SacI endonuclease structural gene and the cell is not of the genus Streptomyces.

18. A cell as in claim 17, wherein the cell is an *E. coli* cell.

19. A DNA molecule comprising a ribosomal protein small subunit 1 (rps 1) promoter operably linked to a heterologous structural gene.

20. The DNA molecule according to claim 19, wherein said heterologous structural gene is the SstI or SacI endonuclease gene.

* * * * *